United States Patent [19]

Kim et al.

[11] 4,374,253

[45] Feb. 15, 1983

[54] METHOD FOR PREPARING 1-ARYL-3-ARYLAMINO-2-PYRAZOLIN-5-ONES FROM N-ARYL-3-ARYLAMINO-3-OXIMINOPROPIONAMIDES

[75] Inventors: Chang-Kyu Kim, Rochester; Cataldo A. Maggiulli, Pittsford, both of N.Y.

[73] Assignee: Eastman Kodak Company, Rochester, N.Y.

[21] Appl. No.: 306,622

[22] Filed: Sep. 28, 1981

[51] Int. Cl.³ .................................................. C07D 231/52
[52] U.S. Cl. ....................................... 548/360; 548/365
[58] Field of Search ........................................ 548/360

[56] References Cited

U.S. PATENT DOCUMENTS

| | | | |
|---|---|---|---|
| 2,343,703 | 3/1944 | Porter et al. | 95/6 |
| 2,600,788 | 6/1952 | Loria et al. | 95/6 |
| 2,865,748 | 12/1958 | Feniak et al. | 96/55 |
| 3,062,653 | 11/1962 | Weissberger et al. | 96/100 |
| 3,254,108 | 5/1966 | Maggiulli et al. | 548/360 |
| 3,419,391 | 12/1968 | Young | 96/56.5 |
| 3,615,506 | 10/1971 | Abbott et al. | 96/56.5 |
| 3,798,234 | 3/1974 | Meier et al. | 260/310 A |
| 3,931,221 | 1/1976 | Meier et al. | 548/360 |
| 3,979,412 | 9/1976 | Arai et al. | 548/360 |
| 4,113,954 | 9/1978 | Tracy et al. | 548/365 |
| 4,345,085 | 8/1982 | Kim et al. | 548/360 |

FOREIGN PATENT DOCUMENTS

| | | |
|---|---|---|
| 817887 | 7/1969 | Canada . |
| 1129333 | 10/1968 | United Kingdom . |
| 1129334 | 10/1968 | United Kingdom . |
| 1134329 | 11/1968 | United Kingdom . |

*Primary Examiner*—Henry R. Jiles
*Assistant Examiner*—Natalia Harkaway
*Attorney, Agent, or Firm*—David F. Janci

[57] ABSTRACT

A method for preparing a 1-aryl-3-arylamino-2-pyrazolin-5-one comprises reacting an N-aryl-3-arylamino-3-oximinopropionamide with an acylating agent in an inert solvent, then heating in contact with a strong acid catalyst and a dehydrating agent in an inert solvent, and then heating in contact with an acid in water and a lower alkanol.

23 Claims, No Drawings

METHOD FOR PREPARING 1-ARYL-3-ARYLAMINO-2-PYRAZOLIN-5-ONES FROM N-ARYL-3-ARYLAMINO-3-OXIMINOPROPIONAMIDES

BACKGROUND OF THE INVENTION

1. Field of the Invention

This invention relates to a method for preparing 2-pyrazolin-5-ones. More particularly, this invention concerns a method for preparing 1-aryl-3-arylamino-2-pyrazolin-5-ones from N-aryl-3-arylamino-3-oximinopropionamides. In one aspect this invention relates to a process for preparing 1-aryl-3-arylamino-2-pyrazolin-5-ones that are particularly useful as color-forming couplers or as intermediates in preparing color-forming couplers which produce dyes in photographic elements.

2. Description Relative to the Prior Art

It is well known in the photographic art to form colored photographic images by means of a coupling reaction between an oxidized primary aromatic amine developing agent and a color-forming coupler. In such processes 2-pyrazolin-5-ones are known to be useful as couplers for forming magenta dyes. Many references describe such use of 2-pyrazolin-5-ones and also describe methods for synthesizing the compounds. See, for example, U.S. Pat. Nos. 4,113,954; 3,798,234; 3,615,506; 3,419,391; 3,062,653; 2,865,748; 2,600,788; and 2,343,703; British Pat. Nos. 1,134,329; 1,129,334; and 1,129,333; and Canadian Pat. No. 817,887, all of which are hereby incorporated herein by reference. Copending U.S. patent application Ser. No. 220,409, filed December 29, 1980, now U.S. Pat. No. 4,345,085 describes a method for preparing 2-pyrazolin-5-ones from 1,2,4-oxadiazoles.

Among the 2-pyrazolin-5-ones, the 1-aryl-3-arylamino-2-pyrazolin-5-ones are particularly useful as couplers or as intermediates in preparing couplers. It is always desirable to have new synthetic routes to such pyrazolones, especially new syntheses which are more efficient and economical than other known methods. The present invention provides such a synthetic route to 1-aryl-3-arylamino-2-pyrazolin-5-ones. The new synthesis involves dehydrative cyclization and rearrangement of N-aryl-3-arylamino-3-(O-acyloximino)propionamides and is not described or suggested in any of the references cited above.

SUMMARY OF THE INVENTION

The invention provides a method for preparing a 1-aryl-3-arylamino-2-pyrazolin-5-one. The method comprises these steps:

(a) An N-aryl-3-arylamino-3-oximinopropionamide, represented by the structural formula

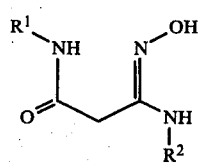

is reacted with an acylating agent in an inert solvent to form an N-aryl-3-arylamino-3-(O-acyloximino)propionamide. In the structural formula above, each of $R^1$ and $R^2$ is phenyl or phenyl substituted with at least one halo, nitro, alkyl, alkoxy, sulfamoyl or substituted sulfamoyl group.

(b) The N-aryl-3-arylamino-3-(O-acyloximino)propionamide is then heated in contact with a strong acid catalyst and a dehydrating agent in an inert solvent to a temperature sufficient to effect dehydrative cyclization and rearrangement thereof to form a 3-(N-acylarylamino)-1-aryl-2-pyrazolin-5-one. In some embodiments of the invention the dehydrating agent of this step is itself an acylating agent. In some preferred embodiments the N-aryl-3-arylamino-3-oximinopropionamide is mixed in step (a) with an amount of acylating agent in excess of the amount needed for step (a), and the excess acylating agent remaining in the reaction solution upon completion of step (a) serves as the dehydrating agent in step (b). Also, there are embodiments in which the strong acid catalyst of step (b) is generated from the dehydrating agent during step (b).

(c) The 3-(N-acylarylamino)-1-aryl-2-pyrazolin-5-one is then heated in contact with an acid in water and a lower alkanol to effect hydrolysis thereof and thereby form the 1-aryl-3-arylamino-2-pyrazolin-5-one.

The method of the present invention is an alternative to pyrazolone syntheses of the prior art and is more efficient and economical than many of the previously known methods. Steps (a) through (c) can be carried out in a single reaction vessel without isolation of any intermediates, so long as the inert solvent is substantially removed from the reaction vessel before carrying out step (c).

DESCRIPTION OF PREFERRED EMBODIMENTS

The 1-aryl-3-arylamino-2-pyrazolin-5-ones produced by the method of the invention are represented by the structural formula:

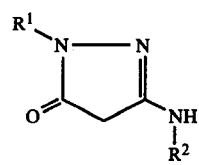

wherein each of $R^1$ and $R^2$ is phenyl or phenyl substituted with at least one halo, nitro, alkyl, alkoxy, sulfamoyl or substituted sulfamoyl group.

Representative $R^1$ and $R^2$ groups include phenyl; a nitrophenyl, such as 4-nitrophenyl and 3-nitrophenyl; a halophenyl, such as 2-chlorophenyl, 2-bromophenyl, 2,4-dichlorophenyl, 2,5-dichlorophenyl, 2,4,5-trichlorophenyl, 2,4,6-trichlorophenyl, 3,5-dibromophenyl, and 4-fluorophenyl; an alkylphenyl, such as 2-methylphenyl and 4-ethylphenyl; an alkoxyphenyl, such as 2-ethoxyphenyl and 4-butoxyphenyl; sulfamoylphenyl; and a substituted sulfamoylphenyl, such as 2-diisopropylsulfamoylphenyl and 4-dimethylsulfamoylphenyl; and combinations thereof, such as 2,6-dichloro-4-methoxyphenyl, 2-chloro-4-nitrophenyl, 2-chloro-5-nitrophenyl, 2,6-dichloro-4-nitrophenyl, and 2-chloro-4-dimethylsulfamoylphenyl.

In certain preferred embodiments of the invention, at least one of $R^1$ and $R^2$ is phenyl substituted with one or two halo groups and a nitro group. Such compounds are particularly useful in making magenta dye-forming couplers.

The N-aryl-3-arylamino-3-oximinopropionamide starting materials for the method of the invention, represented by the structural formula set out in the Summary of the Invention above, are readily prepared by a combination of known chemical reactions. Two such methods for the preparation of the starting materials are syntheses which we refer to as the thioamide route and the imino ether route, respectively.

As an example of the thioamide route of starting material preparation, 3-anilino-3-oximino-N-phenylpropionamide is prepared by the following reaction sequence:

(1) N-phenylacetoacetamide is reacted with phenyl isothiocyanate in the presence of sodium methoxide in a lower alkanol solvent such as methanol or ethanol to give a thioamide derivative, i.e.,

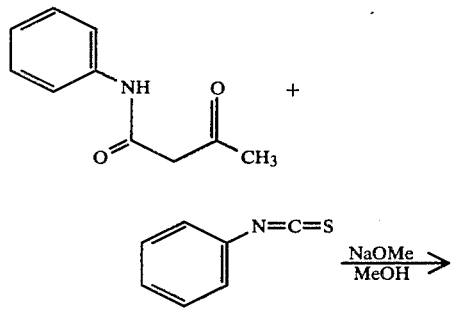

(2) The resulting thioamide is methylated with methyl iodide to give a methylthio derivative, i.e.,

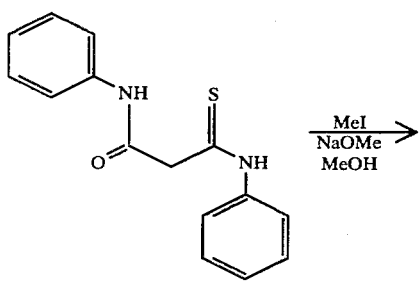

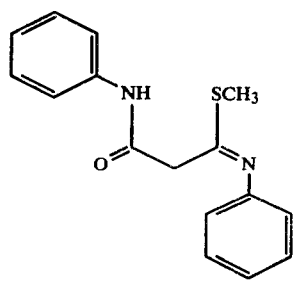

(3) The methylthio compound is then reacted with hydroxylamine in aqueous ethanol to give the desired N-phenylamidoxime, i.e.,

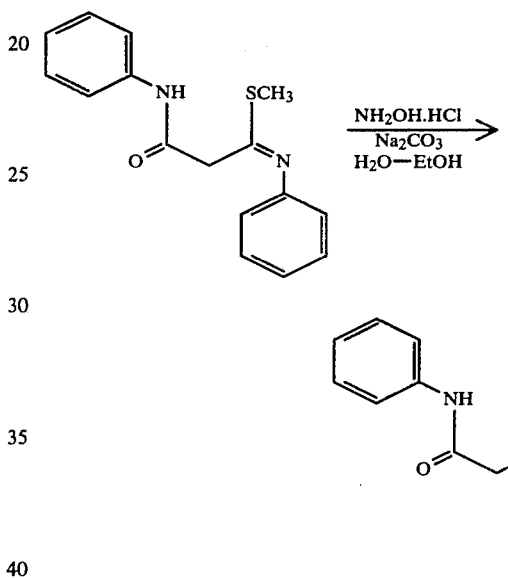

As an example of the imino ether route of starting material preparation, 3-(2-chloro-5-nitroanilino)-3-oximino-N-(2,4,6-trichlorophenyl)-propionamide is prepared by the following reaction sequence:

(1) N-(2,4,6-trichlorophenyl)-2-cyano-acetamide is reacted with ethanol and anhydrous hydrogen chloride at room temperature in a mixture of tetrahydrofuran (THF) and toluene to give 3-ethoxy-3-imino-N-(2,4,6-trichlorophenyl)-propionamide hydrochloride salt, i.e.,

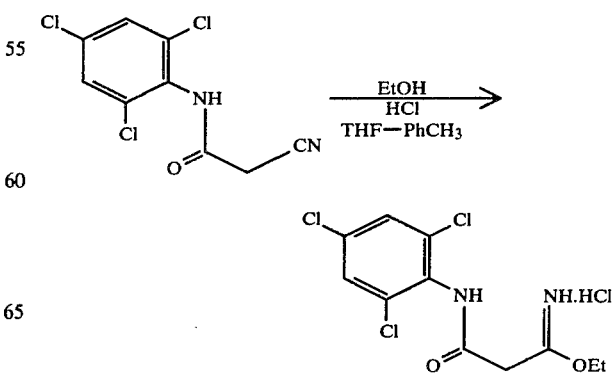

(2) the resulting imino ether hydrochloride is reacted with 2-chloro-5-nitroaniline in methanol at 40° C. to give 3-(2-chloro-5-nitrophenyl)imino-3-methoxy-N-(2,4,6-trichlorophenyl)propionamide, i.e.,

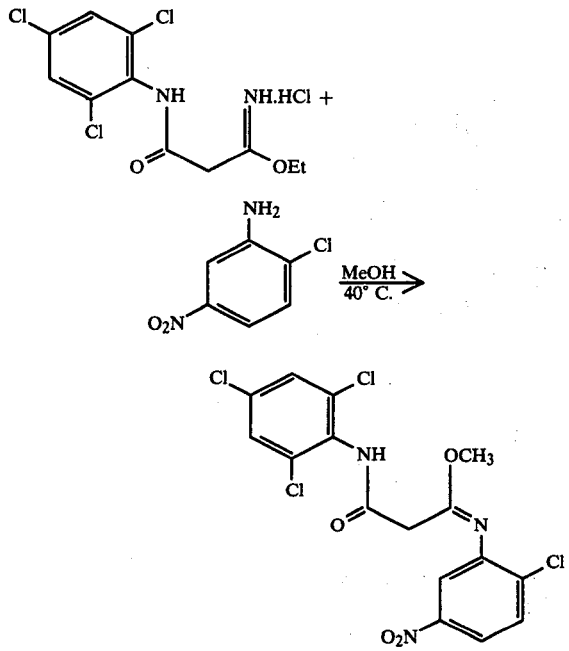

(3) the N-arylimino ether is then heated with hydroxylamine in a mixture of methanol and THF under reflux to give the desired 3-(2-chloro-5-nitroanilino)-3-oximino-N-(2,4,6-trichlorophenyl)-propionamide, i.e.,

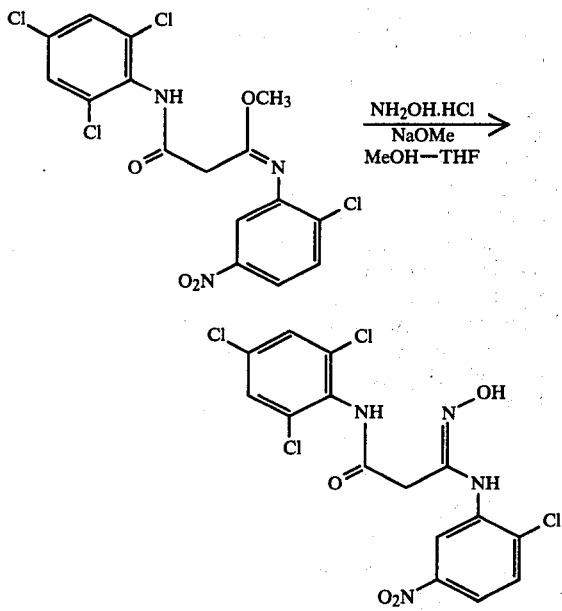

The method of the invention is then used to convert the N-aryl-3-arylamino-3-oximinopropionamide starting material to a 1-aryl-3-arylamino-2-pyrazolin-5-one.

In the first step of the method (designated step (a)), the N-aryl-3-arylamino-3-oximinopropionamide is reacted with an acylating agent to form an O-acyloximino derivative (i.e., an N-aryl-3-arylamino-3-(O-acyloximino)propionamide) in accordance with the following equation:

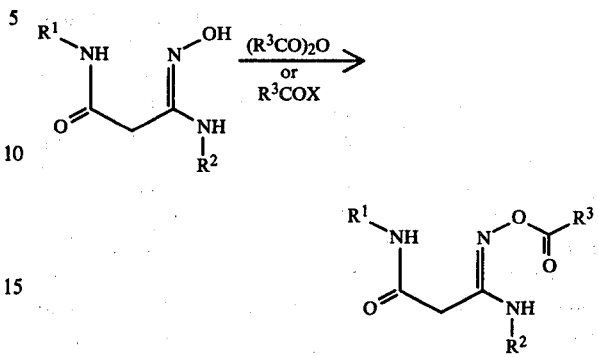

wherein $R^1$ and $R^2$ are as previously defined, $R^3$ is alkyl or aryl, and X is halo.

The acylating agent used in step (a) is preferably an anhydride or an acid halide derived from aliphatic or aromatic (preferably aliphatic) carboxylic acids. Examples of suitable acylating agents are acetic anhydride, acetyl chloride, propionic anhydride, propionyl chloride, benzoic anhydride, and benzoyl chloride.

The step (a) acylation is carried out at ambient temperature in a solvent inert to the acylation reaction. The N-aryl-3-arylamino-3-(O-acyloximino)propionamide thus formed can be isolated in a pure form, if desired. However, isolation is not necessary, because the inert solvent can also be chosen to meet the criteria of step (b) discussed below, and, therefore, step (b) can be carried out using the reaction solution present upon completion of step (a), without isolating the N-aryl-3-arylamino-3-(O-acyloximino)propionamide and dissolving it in another solvent.

Step (b), the next step in the method of the invention, comprises heating the N-aryl-3-arylamino-3-(O-acyloximino)propionamide in contact with a strong acid catalyst and a dehydrating agent in an inert solvent to a temperature sufficient to effect dehydrative cyclization and rearrangement of the N-aryl-3-arylamino-3-(O-acyloximino)propionamide to form acylated pyrazolinone derivatives comprising at least a 3-(N-acylarylamino)-1-aryl-2-pyrazolin-5-one.

As mentioned previously, the same inert solvent can serve as the solvent for both steps (a) and (b). In such a case, in addition to being inert to the reaction of step (a), the solvent is one in which the step (b) reactants are soluble, it is inert to the reaction of step (b), and it has a high boiling point to enable the cyclization reaction of step (b) to be carried out at an elevated temperature (preferably at least about 80° C.), thus facilitating the formation of an intermediary 1,2,4-oxadiazoline ring during the cyclization reaction. Preferable solvents which satisfy the criteria for both steps (a) and (b) have boiling points at or above about 80° C. and are selected from aliphatic caboxylic acids, esters, and nitriles, aromatic hydrocarbons, and halogenated hydrocarbons. Specific examples of preferred inert solvents are acetic acid, propionic acid, n-butylacetate, acetonitrile, butyronitrile, toluene, xylene, chlorobenzene, and trichloroethane.

The strong acid catalyst of step (b) is present in an amount effective to catalyze the cyclization and rearrangement in step (b). It is chosen from the anhydrous strong inorganic and organic acids. Some examples of useful acid catalysts are anhydrous hydrogen chloride, methanesulfonic acid, and p-toluenesulfonic acid.

In some embodiments of the invention, the acid catalyst is not separately added in step (b) but is generated from the dehydrating agent during step (b). Phosphorous oxychloride and thionyl chloride are examples of dehydrating agents that can serve such a dual purpose.

The dehydrating agent of step (b) is present to keep the reaction solution anhydrous by reacting with water formed during the reaction in order to remove it. It also reacts with the alcoholic hydroxyl group in the intermediate 1,2,4-oxadiazoline formed during step (b). The dehydrating agent is added in an amount sufficient to accomplish these purposes. It is chosen to be compatible with the inert solvent and acid catalyst. For example, phosphorous pentoxide is used with anhydrous hydrogen chloride in acetonitrile or butyronitrile but not in acetic acid or propionic acid.

The dehydrating agent in some embodiments is also an acylating agent and is the same as or different from the acylating agent used in step (a). In some preferred embodiments the acylating agent in step (a) is present in an amount in excess of the amount needed for step (a), and the excess acylating agent remaining in the reaction solution upon completion of step (a) serves as the dehydrating agent in step (b). Therefore, in some embodiments the dehydrating agent is chosen from the compounds described above as useful acylating agents for step (a). For example, in some embodiments of the invention acetic anhydride is used in excess as the acylating agent with acetic acid as the solvent in step (a); then in step (b) methanesulfonic acid is added to the solution to serve as the acid catalyst, while the excess acetic anhydride still present serves as the dehydrating agent, and the acetic acid continues to serve as the inert solvent. However, it is also adequate for the dehydrating agent to be a compound other than an acylating agent, in which case it is added separately in step (b).

When the dehydrating agent is other than an acylating agent, step (b) proceeds to form acylated pyrazolinone derivatives in accordance with the following equation:

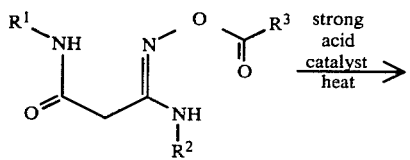

N—aryl-3-arylamino-
3-(O—acyloximino)-
propionamide

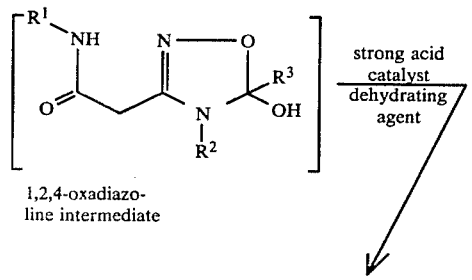

1,2,4-oxadiazo-
line intermediate

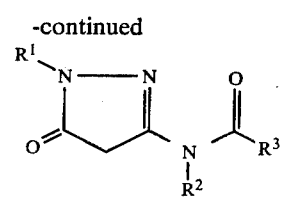

3-(N—acylarylamino)-1-
aryl-2-pyrazolin-5-one wherein $R^1$, $R^2$, and $R^3$ are as previously defined. However, when the dehydrating agent chosen is an acylating agent, the resultant acylated pyrazolinone derivatives comprise a mix of a 3-(N-acylarylamino)-1-aryl-2-pyrazolin-5-one, as represented by the structural formula set out in the equation immediately above, and a 3-(N-acylarylamino)-5-acyloxy-1-arylpyrazole represented by the structural formula:

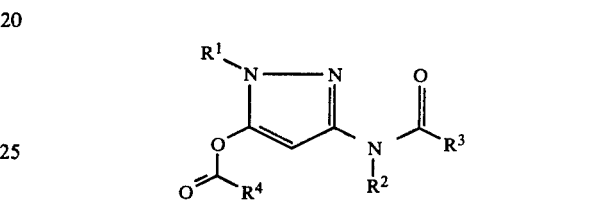

wherein $R^1$, $R^2$, and $R^3$ are as previously defined, and $R^4$ is an alkyl or aryl group. Both of these acylated pyrazolinone derivatives are converted by the subsequent step, designated (c), of the method into the desired 1-aryl-3-arylamino-2-pyrazolin-5-one.

In step (c) the acylated pyrazolinone derivatives are heated in contact with an acid in water and a lower alkanol to effect hydrolysis in order to form the 1-aryl-3-arylamino-2-pyrazolin-5-one. The acid is chosen from those usually employed in acid hydrolysis processes in general, e.g., hydrochloric acid or sulfuric acid. The lower alkanol is an aliphatic alcohol, preferably having from 1 to 4 carbon atoms, e.g., methanol, ethanol or isopropanol. The heating is carried out under reflux at about the boiling point of the particular alkanol being used.

After cooling, the solid 1-aryl-3-arylamino-2-pyrazolin-5-one can be simply collected, washed, and dried.

In preferred embodiments steps (a) through (c) are carried out in a single reaction vessel without isolation of any intermediates. In such cases the inert solvent is substantially removed from the reaction vessel (preferably by vacuum distillation, i.e., distillation under reduced pressure) before carrying out step (c).

The following Examples further illustrate preferred embodiments of the method of the invention.

EXAMPLE I

Preparation of
3-(2-Chloro-5-nitroanilino)-1-(2,4,6-trichlorophenyl)-2-pyrazolin-5-one In a 5 L three-necked flask, equipped with a stirrer, a reflux condenser, and a thermometer, were placed 226 g of 3-(2-chloro-5-nitroanilino)-3-oximino-N-(2,4,6-trichlorophenyl)propionamide, 2 L of glacial acetic acid, and 500 mL of acetic anhydride. The mixture was stirred at room temperature for 18 hours. The yellow color of the slurry turned almost colorless, and thin layer chromatography (TLC) showed that the O-acetyloximino derivative was the sole product. To the reaction mixture was added 50 g of methanesulfonic acid and the mixture was heated as quickly as possible to its boiling point, 117°–120° C., and kept under reflux for 10 minutes. TLC showed that the reaction was essentially complete at that time and gave a mixture of 3-(N-acetyl-2-chloro-5-nitroanilino)-1-(2,4,6-trichlorophenyl)-2-pyrazolin-5-one and 3-(N-acetyl-2-chloro-5-nitroanilino)-5-acetyloxy-1-(2,4,6-trichlorophenyl)-pyrazole. At the end of the heating period, the reflux condenser was quickly replaced with a distillation head, and a water-aspirator vacuum was carefully applied to distill off the solvent as well as to cool down the mixture to 50°–60° C. The distillation of solvent was continued keeping the pot temperature at 50°–60° C. until no more distillate came off. The resulting dark greenish brown viscous oil was dissolved in 2 L of methanol with heat, and 500 mL of concentrated hydrochloric acid in water was added slowly through a dropping funnel. The mixture was heated under reflux for 1 hour, cooled to room temperature, and then allowed to stand at room temperature overnight. The solid was collected, washed with methanol and water, and dried. There was obtained 91 g (42%) of the desired 3-(2-chloro-5-nitroanilino)-1-(2,4,6-trichlorophenyl)-2-pyrazolin-5-one, having a melting point of 278°–280° C.

EXAMPLE II

Preparation of 3-Anilino-1-phenyl-2-pyrazolin-5-one

The process of Example I was followed using 3-anilino-3-oximino-N-phenylpropionamide to provide the corresponding pyrazolinone, mp 220°–223° C.

EXAMPLE III

Preparation of 3-(4-Nitroanilino)-1-(2,4,6-trichlorophenyl)-2-pyrazolin-5-one

The process of Example I was followed using 3-(4-nitroanilino)-3-oximino-N-(2,4,6-trichlorophenyl)propionamide to provide the corresponding pyrazolinone, mp 299°–303° C.

EXAMPLE IV

Preparation of 3-(2,4-Dichloroanilino)-1-(2,6-dichloro-4-nitrophenyl)-2-pyrazolin-5-one The process of Example I was followed using 3-(2,4-dichloroanilino)-3-oximino-N-(2,6-dichloro-4-nitrophenyl)propionamide to provide the corresponding pyrazolinone, mp 228°–231° C.

The invention has been described in detail with particular reference to preferred embodiments thereof, but it should be understood that variations and modifications can be effected within the spirit and scope of the invention.

What is claimed is:

1. A method for preparing a 1-aryl-3-arylamino-2-pyrazolin-5-one, which method comprises the steps of:
   (a) reacting an N-aryl-3-arylamino-3-oximinopropionamide, represented by the structural formula

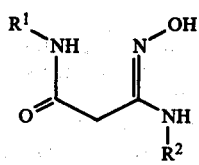

wherein each of $R^1$ and $R^2$ is phenyl or phenyl substituted with at least one halo, nitro, alkyl, alkoxy, sulfamoyl or substituted sulfamoyl group, with an acylating agent in an inert solvent to form an N-aryl-3-arylamino-3-(O-acyloximino)propionamide;
   (b) heating the N-aryl-3-arylamino-3-(O-acyloximino)propionamide in contact with a strong acid catalyst and a dehydrating agent in an inert solvent to a temperature sufficient to effect dehydrative cyclization and rearrangement of the N-aryl-3-arylamino-3-(O-acyloximino)propionamide to form a 3-(N-acylarylamino)-1-aryl-2-pyrazolin-5-one; and
   (c) heating the 3-(N-acylarylamino)-1-aryl-2-pyrazolin-5-one in contact with an acid in water and a lower alkanol to effect hydrolysis of the 3-(N-acylarylamino)-1-aryl-2-pyrazolin-5-one to form the 1-aryl-3-arylamino-2-pyrazolin-5-one.

2. The method of claim 1, wherein at least one of $R^1$ and $R^2$ is phenyl substituted with one or two halo groups and a nitro group.

3. The method of claim 1, wherein the N-aryl-3-arylamino-3-oximinopropionamide is 3-(2-chloro-5-nitroanilino)-3-oximino-N-(2,4,6-trichlorophenyl)propionamide; 3anilino-3-oximino-N-phenylpropionamide; 3-(4-nitroanilino)-3-oximino-N-(2,4,6-trichlorophenyl)propionamide; or 3-(2,4-dichloroanilino)-3-oximino-N-(2,6-dichloro-4-nitrophenyl)propionamide.

4. The method of claim 1, wherein the acylating agent is an anhydride or an acid halide derived from aliphatic or aromatic carboxylic acids.

5. The method of claim 1, wherein the acylating agent is acetic anhydride, acetyl chloride, propionic anhydride, propionyl chloride, benzoic anhydride or benzoyl chloride.

6. The method of claim 1, wherein the inert solvent of step (a) is an aliphatic carboxylic acid, ester, or nitrile; an aromatic hydrocarbon; or a halogenated hydrocarbon.

7. The method of claim 1, wherein the inert solvent of step (a) is acetic acid, propionic acid, n-butyl acetate, acetonitrile, butyronitrile, toluene, xylene, chlorobenzene or trichloroethane.

8. The method of claim 1, wherein the dehydrating agent is an acylating agent.

9. The method of claim 1, wherein the dehydrating agent is an anhydride or an acid halide derived from aliphatic or aromatic carboxylic acids.

10. The method of claim 1, wherein the dehydrating agent is acetic anhydride, acetyl chloride, propionic anhydride, propionyl chloride, benzoic anhydride or benzoyl chloride.

11. The method of claim 1, wherein the N-aryl-3-arylamino-3-oximinopropionamide is mixed in step (a) with an amount of the acylating agent in excess of the amount needed for step (a), and wherein the excess acylating agent serves as the dehydrating agent in step (b).

12. The method of claim 1, wherein the dehydrating agent is phosphorous oxychloride or thionyl chloride, and wherein the strong acid catalyst is generated from the dehydrating agent during step (b).

13. The method of claim 1, wherein the strong acid catalyst is an anhydrous strong acid.

14. The method of claim 1, wherein the strong acid catalyst is anhydrous hydrogen chloride, methanesulfonic acid or p-toluenesulfonic acid.

15. The method of claim 1, wherein the inert solvent of step (b) has a boiling point at or above about 80° C.

16. The method of claim 1, wherein the inert solvent of step (b) is an aliphatic carboxylic acid, ester, or nitrile; an aromatic hydrocarbon; or a halogenated hydrocarbon.

17. The method of claim 1, wherein the inert solvent of step (b) is acetic acid, propionic acid, n-butyl acetate, acetonitrile, butyronitrile, toluene, xylene, chlorobenzene or trichloroethance.

18. The method of claim 1, wherein the inert solvent of step (a) also serves as the inert solvent of step (b).

19. The method of claim 18, wherein the method is carried out in a single reaction vessel and the inert solvent is substantially removed from the reaction vessel before carrying out step (c).

20. The method of claim 18, wherein the dehydrating agent is phosphorous pentoxide, the strong acid catalyst is anhydrous hydrogen chloride, and the inert solvent is acetonitrile or butyronitrile.

21. The method of claim 18, wherein the acylating agent is acetic anhydride, the inert solvent is acetic acid, and the strong acid catalyst is methanesulfonic acid.

22. The method of claim 1, wherein the heating in step (b) is to a temperature of at least about 80° C.

23. The method of claim 1, wherein the acid of step (c) is hydrochloric acid or sulfuric acid, and the lower alkanol is methanol, ethanol or isopropanol.

* * * * *